United States Patent
Rigat et al.

(10) Patent No.: US 6,423,680 B1
(45) Date of Patent: Jul. 23, 2002

(54) INHIBITOR OF PLATELET ACTIVATING FACTOR

(75) Inventors: Brigitte Rigat, Abingdon-Oxon (GB); Denis Reynaud; Don Mahuran, both of Toronto (CA)

(73) Assignee: HSC Research and Development Limited Partnership (CA)

( * ) Notice: Subject to any disclaimer, the term of this patent is extended or adjusted under 35 U.S.C. 154(b) by 0 days.

(21) Appl. No.: 09/183,841

(22) Filed: Oct. 30, 1998

(51) Int. Cl.⁷ .............................................. C07K 14/00
(52) U.S. Cl. .......................................... 514/2; 530/350
(58) Field of Search .............................. 514/25, 460, 2; 536/4.1, 17.2, 17.9; 424/277.1; 435/325, 366; 530/350

(56) References Cited

U.S. PATENT DOCUMENTS 5,486,536 A  *  1/1996  Ward et al. .................. 514/460
5,840,317 A  *  11/1998  Morton ..................... 424/227.1

OTHER PUBLICATIONS

Schroder, et al., "Isolation of cDNA encoding the human Gm2 activator protein", Federation of European Biochemical Societies, vol. 251, pp. 197–200.*

Meirer et al., "The Human GM2 Activator Protein: A substrate specific cofactor of Beta–Hexosaminidase–A", Journal of Biological Chemistry, vol. 266, No. 3, pp. 1879–1897, 1991.*

Kubes, Canadian Journal of Physiology & Pharmaceology, 71:88–97, 1993.

Chao and Olson, Biochemical Journal, 292:617–29, 1993.

Izumi and Shimuzu, Biochimica et BioPhysica Acta, 1259:317–33, 1995.

Smiljanic–Georgijev et al., Biochim. Biophys. Acta, 1339:192–202, 1997.

Laneuville et al., Biochem. J. 295:393–397, 1993.

Reynaud and Pace–Asciak, Prostaglandins Leukot. Essent. Fatty Acids 56:9–12, 1997.

Meier et al., J. Biol. Chem., 266:1879–1887, 1991.

* cited by examiner

Primary Examiner—Karen Cochrane Carlson
(74) Attorney, Agent, or Firm—Woodcock Washburn LLP

(57) ABSTRACT

An anti-inflammatory composition is provided. The composition comprises $GM_2$ activator protein or a peptide derived from the $GM_2$ activator protein which is capable of inhibiting platelet activating factor (PAF). The composition is useful in the treatment of inflammatory conditions such as inflammatory bowel disease and asthma.

11 Claims, 3 Drawing Sheets

FIGURE 1

| | | | | |
|---|---|---|---|---|
| MQSLMQAPLL | IALGLLLATP | AQAHLKKPSQ | LSSFSWDNCD | 40 |
| EGKDPAVIRS | LTLEPDPIVV | PGNVTLSVVG | STSVPLSSPL | 80 |
| KVDLVLEKEV | AGLWIKIPCT | DYIGSCTFEH | FCDVLDMLIP | 120 |
| TGEPCPEPLR | TYGLPCHCPF | KEGTYSLPKS | EFVVPDLELP | 160 |
| SWLTTGNYRI | ESVLSSSGKR | LGCIKIAASL | KGI | 193 |

FIGURE 2

| | | | | |
|---|---|---|---|---|
| MRGSHHHHHH | GSIEGRSSFS | WDNCDEGKDP | AVIRSLTLEP | 40 |
| DPIVVPGNVT | LSVVGSTSVP | LSSPLKVDLV | LEKEVAGLWI | 80 |
| KIPCTDYIGS | CTFEHFCDVL | DMLIPTGEPC | PEPLRTYGLP | 120 |
| CHCPFKEGTY | SLPKSEFVVP | DLELPSWLTT | GNYRIESVLS | 160 |
| SSGKRLGCIK | IAASLKGI | | | 178 |

US 6,423,680 B1

SEQUENCE LISTING

```
<160> NUMBER OF SEQ ID NOS: 4

<210> SEQ ID NO 1
<211> LENGTH: 193
<212> TYPE: PRT
<213> ORGANISM: Homo sapiens
<220> FEATURE:
<221> NAME/KEY: SIGNAL
<222> LOCATION: (33)..(55)
<220> FEATURE:
<223> OTHER INFORMATION: residues 56-63 are included in a further
      precursor form of the protein

<400> SEQUENCE: 1

Met Gln Ser Leu Met Gln Ala Pro Leu Leu Ile Ala Leu Gly Leu Leu
  1               5                  10                  15

Leu Ala Thr Pro Ala Gln Ala His Leu Lys Lys Pro Ser Gln Leu Ser
                 20                  25                  30

Ser Phe Ser Trp Asp Asn Cys Asp Glu Gly Lys Asp Pro Ala Val Ile
             35                  40                  45

Arg Ser Leu Thr Leu Glu Pro Asp Pro Ile Val Val Pro Gly Asn Val
         50                  55                  60

Thr Leu Ser Val Val Gly Ser Thr Ser Val Pro Leu Ser Ser Pro Leu
 65                  70                  75                  80

Lys Val Asp Leu Val Leu Glu Lys Glu Val Ala Gly Leu Trp Ile Lys
                 85                  90                  95

Ile Pro Cys Thr Asp Tyr Ile Gly Ser Cys Thr Phe Glu His Phe Cys
            100                 105                 110

Asp Val Leu Asp Met Leu Ile Pro Thr Gly Glu Pro Cys Pro Glu Pro
        115                 120                 125

Leu Arg Thr Tyr Gly Leu Pro Cys His Cys Pro Phe Lys Glu Gly Thr
    130                 135                 140

Tyr Ser Leu Pro Lys Ser Glu Phe Val Val Pro Asp Leu Glu Leu Pro
145                 150                 155                 160

Ser Trp Leu Thr Thr Gly Asn Tyr Arg Ile Glu Ser Val Leu Ser Ser
                165                 170                 175

Ser Gly Lys Arg Leu Gly Cys Ile Lys Ile Ala Ala Ser Leu Lys Gly
            180                 185                 190

Ile

<210> SEQ ID NO 2
<211> LENGTH: 178
<212> TYPE: PRT
<213> ORGANISM: Artificial Sequence
```

-continued

```
<220> FEATURE:
<223> OTHER INFORMATION: His tag at residues 1 to 17
<220> FEATURE:
<223> OTHER INFORMATION: Description of Artificial Sequence: amino acid
      sequence of GM2 protein using His6 tag

<400> SEQUENCE: 2

Met Arg Gly Ser His His His His His His Gly Ser Ile Glu Gly Arg
  1               5                  10                  15

Ser Ser Phe Ser Trp Asp Asn Cys Asp Glu Gly Lys Asp Pro Ala Val
             20                  25                  30

Ile Arg Ser Leu Thr Leu Glu Pro Asp Pro Ile Val Val Pro Gly Asn
         35                  40                  45

Val Thr Leu Ser Val Val Gly Ser Thr Ser Val Pro Leu Ser Ser Pro
     50                  55                  60

Leu Lys Val Asp Leu Val Leu Glu Lys Glu Val Ala Gly Leu Trp Ile
 65                  70                  75                  80

Lys Ile Pro Cys Thr Asp Tyr Ile Gly Ser Cys Thr Phe Glu His Phe
                 85                  90                  95

Cys Asp Val Leu Asp Met Leu Ile Pro Thr Gly Glu Pro Cys Pro Glu
            100                 105                 110

Pro Leu Arg Thr Tyr Gly Leu Pro Cys His Cys Pro Phe Lys Glu Gly
        115                 120                 125

Thr Tyr Ser Leu Pro Lys Ser Glu Phe Val Val Pro Asp Leu Glu Leu
    130                 135                 140

Pro Ser Trp Leu Thr Thr Gly Asn Tyr Arg Ile Glu Ser Val Leu Ser
145                 150                 155                 160

Ser Ser Gly Lys Arg Leu Gly Cys Ile Lys Ile Ala Ala Ser Leu Lys
                165                 170                 175

Gly Ile

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:Novel
      sequence

<400> SEQUENCE: 3

Gly Ser Ile Glu Gly Arg
  1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:Novel
      sequence

<400> SEQUENCE: 4

Trp Ser Cys Pro Val Gly Ser Pro Pro Gly Thr Thr Ala
  1               5                  10
```

INHIBITOR OF PLATELET ACTIVATING FACTOR

FIELD OF THE INVENTION

The present invention relates to anti-inflammatory compositions. More particularly, the present invention relates to an anti-inflammatory composition comprising $GM_2$ activator protein.

BACKGROUND OF THE INVENTION

Inflammation is generally a protective response triggered by tissue injury or destruction. It is characterized physically by pain, heat, redness, swelling and loss of function, and histologically by a complex series of events which include dilatation of arterioles, leakage in capillaries and venules, exudation of plasma and other fluids, and migration of leukocytes into the inflammatory focus. Although characterized as a protective response, disorders exist in which prolonged or chronic inflammation is undesirable because it causes extreme discomfort as well as extensive tissue damage. Examples of such inflammatory disorders include autoimmune disease, hypersensitivity, rheumatism (such as rheumatoid arthritis), vasculitis, asthma, allergies, rhinitis, gout and tissue-specific conditions such as glomerulonephritis and hepatitis.

Many "anti-inflammatory" drugs exist today which are used to treat the symptoms associated with inflammatory disorders. Treatments including both steroidal and non-steroidal (NSAIDS) drugs are known. Unfortunately, undesirable side effects are commonly encountered with the use of either of these treatments. NSAIDS, such as the salicylates and related compounds, for example, exhibit toxicity, and can cause gastric and intestinal ulceration, disturbances in platelet function and changes in renal function. Steroidal treatments also exhibit toxicity, and have been found to adversely effect infant growth, development and immune response, and cause bone fragility in older patients.

There exists a need, thus, to develop compounds useful to treat inflammation which are non-toxic, present with less severe side effects and which are more efficacious than existing therapies. In this regard, it would be highly desirable to develop an anti-inflammatory derived from a naturally-occurring compound native to the mammalian system.

During the past two decades, studies describing the chemistry and biology of PAF (platelet activating factor) have been extensive. This potent phosphoacylglycerol exhibits a wide variety of physiological and pathophysiological effects in various cells and tissues. PAF acts, through specific receptors and a variety of signal transduction systems, to elicit diverse biochemical responses (Chao and Olson, Biochemical Journal, 292:617–29, 1993). The role of PAF in the inflammatory response is particularly important. It is believed to promote adhesion of polymorphonuclear leukocytes (PMNs) to the endothelium at a site of inflammation and subsequent migration of PMNs through the endothelial barrier, both of which are crucial steps in an inflammatory response.

PAF, along with cytokines such as the interleukins, tumor necrosis factor and others, appear to be involved in the inflammation that is associated with inflammatory bowel diseases such as Crohn's disease, ulcerative colitis, ischemic colitis, or antibiotic-associated colitis (Kubes, Canadian Journal of Physiology & Pharmacology, 71:88–97, 1993). PAF is also one of the chemical mediators that may participate in the inflammatory process underlying asthma.

Inhibitors of PAF have been developed as potential therapeutics for the treatment and management of such inflammatory diseases. However, most PAF inhibitors are directed at receptors of PAF rather than PAF itself (Chao and Olson,supra; Izumi and Shimizu, Biochimica et Biophysica Acta, 1259:317–33,1995). Such inhibitors have been found to lack efficacy due to receptor-heterogeneity and, thus, inhibit only a subset of PAF receptors.

SUMMARY OF THE INVENTION

The $GM_2$ activator protein, a substrate specific cofactor for the enzyme, lysosomal beta-hexosaminidase A (Hex A), which catalyzes the hydrolysis of $GM_2$ ganglioside ($GM_2$), has now been found to inhibit PAF by directly binding thereto.

Accordingly, in one aspect of the present invention, there is provided an anti-inflammatory composition comprising $GM_2$ activator protein, or a $GM_2$ activator peptide derived therefrom, in combination with at least one pharmaceutically acceptable carrier.

In another aspect of the present invention there is provided a method of treating an inflammatory condition in a mammal comprising administering to said mammal a therapeutically effective amount of a composition comprising $GM_2$ activator protein, or a $GM_2$ activator peptide derived therefrom, and at least one pharmaceutically acceptable carrier.

In a further aspect of the present invention, an article of manufacture is provided comprising packaging material and a pharmaceutical composition contained within said packaging material, wherein said pharmaceutical composition is therapeutically effective to reduce inflammation in the body of a mammal, and wherein the packaging material comprises a label which indicates that the composition can be used to reduce inflammation, said composition comprising $GM_2$ activator protein, or a $GM_2$ activator peptide derived therefrom, and at least one pharmaceutically acceptable carrier.

Embodiments of the present invention are described in greater detail with reference to the accompanying drawings in which:

BRIEF DESCRIPTION OF THE DRAWINGS

FIG. 1 is the amino acid sequence of human $GM_2$ activator protein (SEQ ID NO: 1);

FIG. 2 is the amino acid sequence of $GM_2$ activator protein (SEQ ID NO: 2) prepared using the $His_6$-tag bacterial expression system as described herein;

DETAILED DESCRIPTION OF THE INVENTION

Figure 3:
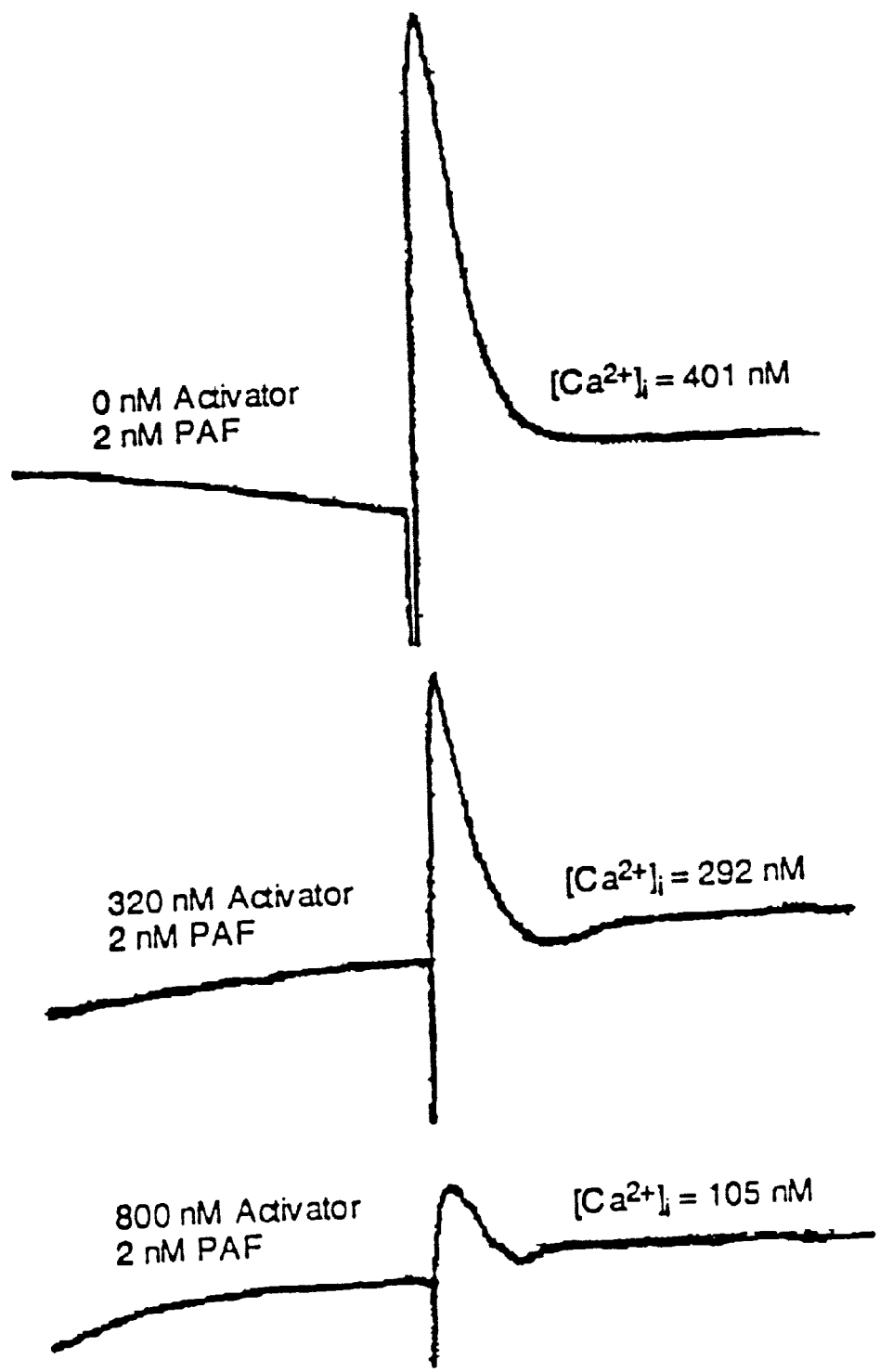
FIG. 3 illustrates spectrographic results from a calcium release assay.

An anti-inflammatory composition is provided comprising $GM_2$ activator protein, or an effective $GM_2$ activator peptide derived from said protein, in combination with at least one pharmaceutically acceptable carrier.

The term "anti-inflammatory" is meant to refer to the ability of the GM 2 activator protein to inhibit PAF so as to prevent, or at least reduce, undesired inflammatory response including, but not strictly limited to, responses such as redness, swelling, pain and PMN accumulation at the inflammatory site and other associated cellular responses. Inhibition of PAF is determined by an appropriate assay such as the calcium release assay which is described in detail in the specific examples herein.

With reference to $GM_2$ activator protein, the term "an effective $GM_2$ activator peptide" is meant to refer to peptides derived, either in whole or in part, from the sequence of the $GM_2$ activator protein as it is set out in FIG. 1, including modified forms of the $GM_2$ activator protein as well as truncated peptide forms of the protein. Such peptides must be effective to inhibit PAF as set out above.

The $GM_2$ activator protein is a heat stable, protease-resistant, monomeric, lysosomal protein of approximately 22 kDa. Human $GM_2$ activator protein is synthesized as a precursor polypeptide having 193 amino acid residues, as shown in FIG. 1 (SEQ ID NO: 1), of which the first 23 residues represent a signal peptide. The mature protein comprises 162 amino acid residues. It has a single N-linked glycosylated site at the asparagine residue at position 63, and disulfide linkages at each of its 8 cysteine residues.

Effective $GM_2$ activator peptides derived from the parent $GM_2$ activator protein will comprise at least a portion of the $GM_2$ activator protein amino acid sequence, and more notably, the portion of the $GM_2$ activator protein responsible for inhibiting PAF, and comprising that portion which binds to PAF. The $GM_2$ activator peptide may be a mutated form of the wild-type $GM_2$ activator protein in which one or more amino acids are added, deleted, replaced or modified. A $GM_2$ activator peptide in accordance with the present invention may, for example, be a truncated form of the protein comprising only a region of the carboxy-terminus of the $GM_2$ activator protein, in whole or in part, including residues in the region from about 80–193, and particularly residues 83 and 185.

It will be appreciated by those of skill in the art that modifications may be made to the $GM_2$ activator protein or peptides derived therefrom which will not adversely effect their ability to inhibit PAF. Accordingly, additional amino acid residues may be added to the protein which do not alter its activity. For example, protective flanking sequences may be added to the N- or C-terminal ends of the protein or peptide of the present invention in order to prevent degradation thereof that may result from enzymatic, chemical or biochemical attack on administration. Likewise, one or more of the amino acids may be deleted from the protein or peptide, such as a terminal amino acid, without compromising activity.

Alternatively, amino acids native to the protein may be replaced or modified. Conservative amino acid replacement, e.g. replacement of an amino acid within the protein with an amino acid of similar charge and size such as replacement of threonine with serine, can be effected without loss of activity. Non-conservative amino acid replacements may be tolerated, particularly in regions of the protein which are not crucial to its inhibition of PAF. Further, amino acids of the present protein or peptide can be modified or derivatized without adverse effect on activity. In this regard, modifications to the termini may be made to protect the protein or peptide from degradation as set out above. Such modifications may include alkylation of either termini with $C_1$–$C_5$ branched or unbranched alkyl groups, acylation with acyl groups such as formyl, acetyl, and substituted forms thereof including acetamidomethyl (Acm). Amide-forming amino groups such as primary amines (—$NH_2$), and mono- and di-alkylamino groups such as methylamino, ethylamino, dimethylamino, diethylamino, methylethylamino and the like are useful to protect to the C-terminus of the protein or peptide. Desamino and descarboxylated analogs of amino acids are also useful to protect the N- and C-termini, respectively, either coupled thereto or used in place of the native terminal amino acid. Internal amino acids of the protein or peptide can also be modified by derivatization without affecting activity. Such derivatizations can be made to the side chains of the amino acids. For example, the side chains can be derivatized by incorporation of protective groups such as those described above.

Another modification that may be incorporated in the $GM_2$ activator protein or peptides of the present invention is cyclization. Cyclization can be effected between both terminal and internal amino acid residues via disulfide linkages, for example, between two cysteine residues, or via peptide linkages between the amino and carboxyl groups of terminal amino acid residues or of side chains of terminal or internal amino acid residues.

Other modifications can be incorporated into the present protein or peptides without adversely affecting activity, including, but not limited to, substitution of one or more of the amino acids in the natural L-isomeric form with amino acids in the D-isomeric form. Thus, the protein or peptide may include one or more D-amino acid residues, or may comprise amino acids which are all in the D-form.

Acid addition salts of the present compounds are also contemplated. Thus, $GM_2$ activator protein or peptide may be treated with an inorganic acid such as hydrochloric, hydrobromic, sulfuric, nitric, phosphoric, and the like, or an organic acid such as acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic, salicylic and the like, to provide a water soluble salt that is suitable for use in the present anti-inflammatory compositions.

The $GM_2$ activator protein or peptide for use in the present composition may be synthetically-derived using established recombinant methods. Such methods generally entail transformation of a suitable prokaryotic or eukaryotic host cell with a vector having inserted expressibly therein the DNA sequence encoding the $GM_2$ activator protein. Recombinant $GM_2$ activator protein may be derived from any suitable prokaryotic source including bacterial sources such as E. coli and B. subtilis, fungal sources such as Aspergillus nidulans and Aspergillus niger and yeast sources. Eukaryotic cell lines may also be employed to produce $GM_2$ activator protein including insect cell lines such as Spodoptera frugiperda and mammalian cell lines such as Chinese hamster ovary cells (CHO cells) for example of K1 lineage (ATCC CCL 61) including the Pro5 variant (ATCC CRL 1281); fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including HeLa lineage (ATCC CCL 2) and neuroblastoma cells of the lines IMR-32 (ATCC CCL 127), SK-N-MC (ATCC HTB 10) and SK-N-SH (ATCC HTB 11).

As will be appreciated by one of skill in the art, depending on the source, the human $GM_2$ activator protein may or may not be modified post-translationally, and thus may or may not be glycosylated so as to be in the form in which it naturally exists in humans. Generally, $GM_2$ activator protein produced from mammalian cell lines is glycosylated, while GM$_2$ activator protein produced from bacterial sources will be non-glycosylated. Yeast, fungal and insect cell sources of GM$_2$ activator protein will produce GM$_2$ activator protein which is at least partially glycosylated. It is noted, however, that glycosylation is not necessary to yield an active GM$_2$ activator protein or peptide in accordance with the present invention.

Other methods of obtaining GM$_2$ activator protein or peptide may also be used. For example, GM$_2$ protein may be isolated from tissue samples using techniques of isolation and purification well-known by those of skill in the art. GM$_2$ activator protein, and more appropriately peptides derived therefrom, can also be prepared using well-established solid-phase peptide synthesis as described by Stewart et al. in Solid Phase Peptide Synthesis, 2$^{nd}$ Edition, 1984, Pierce Chemical Company, Rockford, Illinois, and as described by Bodanszky and Bodanszky in The Practice of Peptide Synthesis, 1984, Springer-Verlag, New York. Examples of solid phase peptide synthesis methods include the BOC method which utilizes t-butyloxycarbonyl as the a-amino protecting group, and the FMOC method which utilizes 9-fluorenylmethyloxycarbonyl to protect the a-amino of the amino acid residues, both methods of which are well-known by those of skill in the art.

To ensure that the GM$_2$ activator protein or peptide obtained from either the chemical or biological synthetic techniques described above is the desired protein or peptide, analysis of its composition should be conducted. Such amino acid composition analysis may be conducted using high resolution mass spectrometry to determine the molecular weight of the protein. Alternatively, or additionally, the amino acid content of the protein or peptide can be confirmed by hydrolyzing in aqueous acid, and separating, identifying and quantifying the components of the mixture using HPLC, or an amino acid analyzer. Protein sequenators, which sequentially degrade the protein and identify the amino acids in order, may also be used to determine definitively the sequence of the protein or peptide.

Prior to its use to treat inflammation, the GM$_2$ activator protein or peptide is purified to remove contaminants. In this regard, it will be appreciated that the peptide will be purified so as to meet the standards set out by appropriate regulatory agencies. Any one of a number of conventional purification procedures may be used to attain the required level of purity including, for example, reversed-phase high-pressure liquid chromatography (HPLC) or ion-exchange chromatography.

According to one aspect of the present invention, anti-inflammatory compositions comprising GM$_2$ activator protein or an effective GM$_2$ activator peptide derived therefrom, are prepared for use in treating mammals inflicted with an inflammatory condition or disease. The present composition is particularly suitable for treating inflammatory conditions arising from inflammatory bowel disease, auto-immune disease such as lupus, rhinitis, gout, rheumatism such as rheumatoid arthritis, vasculitis and lung immune disorders such as asthma, allergies, hypersensitivity and infection. The term "mammal" as it is used herein is meant to encompass humans, domestic animals such as cats, dogs and horses, livestock such as cattle, pigs, goats, and sheep, and non-domesticated mammals that may be in need of anti-inflammatory treatment.

The present anti-inflammatory compositions comprise GM$_2$ activator protein or peptide together with a pharmaceutically acceptable carrier. In this context, the term "pharmaceutically acceptable" means acceptable for use in the pharmaceutical and veterinary arts, i.e. a carrier which is non-toxic and which does not adversely affect the activity of the protein or peptide as an anti-inflammatory agent. Pharmaceutically acceptable carriers useful to prepare compositions for in vivo administration include conventional carriers used in formulating protein-based drugs, such as diluents, excipients and the like. Reference may be made to "Remington's Pharmaceutical Sciences", 17th Ed., Mack Publishing Company, Easton, Penn., 1985, for guidance on drug formulations generally. As will be appreciated, the pharmaceutical carriers used to prepare compositions in accordance with the present invention will depend on the administrable form to be used to treat the inflicted mammal.

According to one embodiment of the invention, the present composition will be formulated for oral administration. In this regard, the composition may be in liquid or powder form, i.e. freeze-dried, encapsulated or prepared into tablets for sustained-release in the intestine. Other formulations of the present composition are also contemplated. Preparation of the composition into a suppository may also be useful, particularly in the treatment of inflammatory bowel disease, for its delivery directly into the intestine. Alternatively, the present composition may be prepared for use as an aerosol in the treatment of the inflammatory condition of asthma.

In another aspect of the present invention, a method for treating individuals with an inflammatory disease condition is provided comprising administration of an anti-inflammatory amount of the present composition. In this regard, an "anti-inflammatory amount" is an amount suitable to inhibit PAF, thereby resulting in preventing or at least reducing the occurrence of the inflammatory response in any one or more of its forms as previously set out. Precise dosage sizes of the composition appropriate for treatment are established in appropriately controlled clinical trials, and will correspond to an amount of protein or peptide that reduces inflammation, as determined by the inhibition of PAF, without causing intolerable side effects. It is anticipated that an effective treatment regimen for patients will involve the administration of dosages in the range of 1–100 mg, and more specifically, dosages in the range of 3–30 mg. It will be appreciated, however, that the exact dosage sizes required to attain the desired anti-inflammatory effect will vary with a number of factors including the route and frequency of administration, the inflammatory condition and the with the individual being treated.

For use in treating inflammation in a mammal including a human, the present invention provides, in another of its aspects, a package, in the form of a sterile-filled vial or ampoule, that contains an anti-inflammatory amount of a GM$_2$ protein or peptide in accordance with the present invention, in either unit dose or multi-dose amounts, wherein the package incorporates a label instructing use of its contents for treating inflammation. In one embodiment of the invention, the package contains the peptide and the desired carrier, as an administration-ready formulation, for example, in the form of capsules. Alternatively, and according to another embodiment of the invention, the package provides the anti-inflammatory peptide in a form, such as a lyophilized form, suitable for reconstitution in a suitable carrier, such as phosphate-buffered saline.

Embodiments of the present invention are described by reference to the following specific examples which are not to be construed as limiting.

Example 1

Preparation of the GM$_2$ Activator Protein

The GM$_2$ activator protein was prepared using the His$_6$-tag bacterial expression system as described by Smiljanic- Georgijev et al. (Biochim. Biophys. Acta, 1339:192–202, 1997). A non-glycosylated $GM_2$ activator protein was expressed from this system having the amino acid sequence set out in FIG. 2 (SEQ ID NO: 2). As can be seen by reference to FIG. 2 (SEQ ID NO: 2), the $His_6$ extension used in this case included the additional residues, —GSIEGR— (SEQ ID NO: 3), which define a Factor X cleavage site, the cleavage site of a blood-clotting enzyme, to allow removal of the $His_6$ extension, if necessary. With respect to the purification of the expressed protein, it is noted that the $His_6$ extension binds $Ni^{+2}$-containing resin (e.g. Ni-NTA). Thus, purification of the protein was readily conducted using such a resin.

A non-functional, truncated form of the activator was also prepared for use as a negative control in the present experiments. This truncated form comprised, in sequence, the $His_6$ extension, the Factor X cleavage site, residues 32–157 of the native $GM_2$ activator protein, and the C-terminal sequence,—WSCPVGSPPGTTA-(SEQ ID NO: 4) as a result of a frameshift.

Example 2

Calcium Release Assay

Neutrophils were isolated from heparinized venous blood collected from healthy volunteers as previously reported (Laneuville et al., Biochem. J. 295:393–397, 1993). Neutrophils (1 ml, $10^7$ cells) were loaded with a 3 mM solution of a fluorescent dye, INDO-1 AM (Calbiochem.) for use in calculating $[Ca^{2+}]_i$ as previously reported (Laneuville et al., supra; Reynaud and Pace-Asciak, Prostaglandins Leukot. Essent. Fatty Acids 56:9–12,1997). For each measurement, $2 \times 10^6$ cells were used in 1 ml of cell medium in a temperature-controlled (37° C.) plastic cuvette with continuous stirring. Varying concentrations of functional $GM_2$ activator protein and non-functional truncated $GM_2$ activator protein (i.e. 0, 0.32 and 0.8 nmol) were added to individual cuvettes. Following equilibration of the assay mix, PAF (0.002 nmol) was added and the increase in $[Ca^{2+}]_i$ calculated by a determination of fluorescence. Fluorescence was measured using a Perkin-Elmer fluorescence spectrophotometer as previously reported (Reynaud and Pace-Asciak, supra).

The results of the calcium release assay are shown in FIG. 3. The addition of extracellular functional and non-functional activator protein to a suspension of INDO-1 AM-loaded cells did not result in a change in $[Ca^{2+}]_i$. The addition of 2 pmol of PAF to the cuvette containing 0 nmol of the functional activator increased the $[Ca^{2+}]_i$ by 401 nM. However, addition of PAF to cuvettes containing the functional activator exhibited a significant decrease in the release of intracellular calcium pools into the cytosol. The PAF-response was inhibited by 75% when 800 pmol (15 µg/ml) of activator was present, but not at all in the presence of 800 pmol of the non-functional truncated activator.

Example 3

Determination of $Gm_2$ Activator Protein Ligand Binding

The ability of the activator protein to bind $GM_2$ ganglioside, PAF, N-formyl-Met-Leu-Phe (fMLP), or leukotriene $B_4$ ($LTB_4$) was assessed using a fluorescence dequenching assay. This assay was first used to evaluate the ability of the activator to transport a self-quenching fluorescence dye, R-18 (octadecylrhodamine conjugated to a saturated C-18 hydrocarbon chain) (obtained from Molecular Probes), between labeled and unlabeled liposomes (phosphatidylcholine containing large unilamellar vesicles, $PC$-$LUV_8$). An increase in fluorescence over time when the activator protein and unlabeled liposomes were admixed with R-18 labeled liposomes indicates the ability of the activator to transport the R-18 dye, the fluorescence of which is proportional to concentration of dye that is transported to the unlabelled liposomes. The assay was then used to determine the protein's ability to bind various ligands by assessing whether each of the compounds identified above inhibits the transport process (Smiljanic-Georgijev et al., supra). In this aspect of the experiment, each compound was added to a mixture of activator protein and unlabeled liposomes prior to the addition of R-18 labeled liposomes as described above.

The R-18 labeled liposomes were prepared as follows. In a total volume of 0.5 ml of NHE buffer, the PC-LUV, (0.44 µmol) were rapidly and thoroughly mixed at room temperature with 0.04 µmol of R-18 (20 mM in 100% ethanol). The mixture was then incubated, in an area protected from light, for 15 min. with gentle mixing. Free R-18 was removed by Sephadex G-50 gel filtration on a 1×4 cm column. The column was then eluted with NHE buffer to yield a quantity of labeled liposomes sufficient for 10 assays.

In each fluorescence dequenching assay, 5 µg of activator protein was mixed with 630 nmol of unlabeled liposomes. The assay was initiated by the addition of 44 nmol of R-18 labeled liposomes. The assay mixture was made up to 1 ml with SPM buffer (0.25 M sucrose, 10 mM $NaH_2PO_4$ buffer, 1 mM $MgCl_2$, pH 5). The mixture was allowed to incubate at 37° C. for 5 min. to allow the reagents to equilibrate. The rate of increase in fluorescence emission was then determined by monitoring at 590 nm, using an excitation wavelength of 560 nm, on a 650–40 fluorometer (Perkin-Elmer). All assays were conducted in a thermostatted (37° C.) quartz cell. Using this assay, the activator protein was found to transport R-18 between labeled and unlabeled liposomes as determined by an increase in fluorescence over time.

In determining binding of the activator to the ligand compounds identified above, a ligand solution was prepared by dissolving the dried ligand material in chloroform:methanol (2:1) to a concentration of 1.3 nmol in 2 µl. This was then added to the mixture of unlabeled liposomes and activator. The solution was thoroughly mixed to allow the ligand to distribute itself between the liposomes and/or activator. To controls containing no activator, 2 µl of chloroform:methanol (2:1) was added. The assay was then conducted as described above by addition of labeled liposomes.

The fluorescence dequenching of the R-18 liposome preparations was measured and calculated as follows. The fluorescence intensity, 5 min. after addition of R-18 $PC$-$LUV_s$, was taken as $F_0$. At the end of the reaction, 60 µl of 20% v/v Triton X-100 was added to the assay mixture to obtain the fluorescence value at infinite dilution of the probe ($F_{100}$). Fluorescence was taken at any time point ($F_t$) and dequenching calculated as:

% R-18 dequenching=100 $(F_t-F_0)/F_{100}$

The fluorescence dequenching units ($F_u$) were calculated by subtraction of the baseline percentage of R-18 fluorescence dequenching (obtained from the sample containing all assay components except the activator) from each sample. Slopes, $[\Delta F_u/\Delta T \text{ (min)}]$, were calculated by subtraction of the baseline slope from the slope of each sample.

Figure 4:
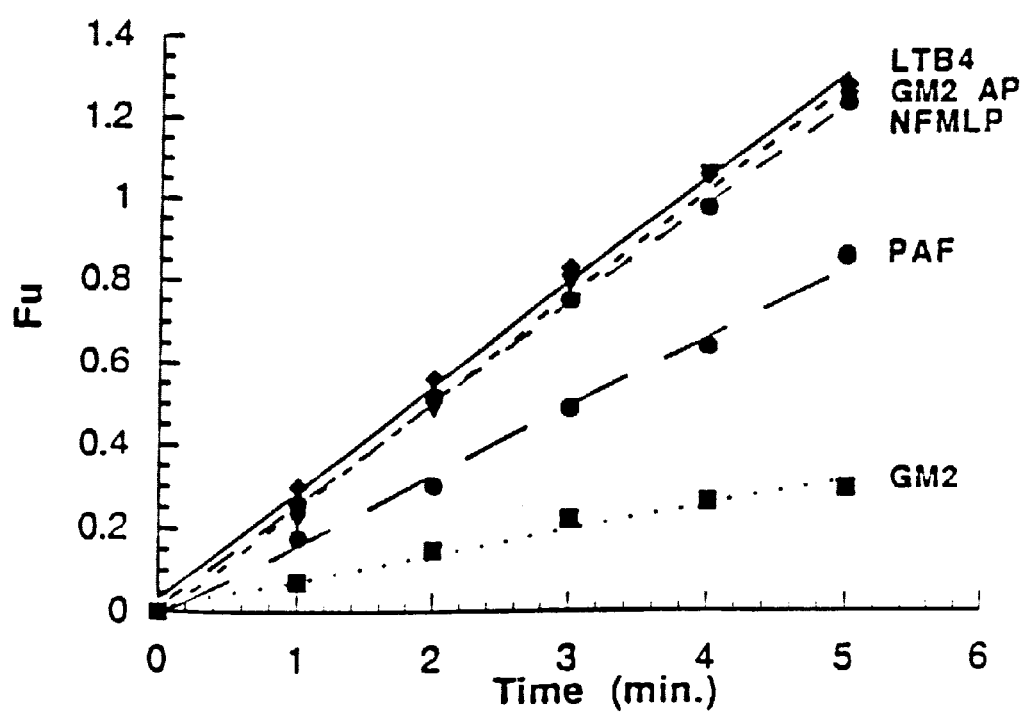
FIG. 4 illustrates a graph of the results obtained in a fluorescence dequenching assay.

The results of this experiment illustrate, as shown in FIG. 4, that a mixture of activator in the absence of a ligand compound produced a slope of 0.256 $\Delta F_u/\Delta T(\text{min})$. A similar slope was produced when the activator was admixed with LTB$_4$ and fMLP. Activator in the presence of PAF produced a lower slope of 0.168, however, while activator in the presence of GM$_2$ produced a lower slope of 0.060. Thus, GM$_2$ and PAF were found to inhibit the activator's transfer of R-18 between liposomes. PAF inhibited R-18 transport by 34% while GM$_2$ inhibited R-18 transport by 77%.

Example 4

Comparative Experiment

The conventional biological assay for the GM$_2$ activator involves its function as a substrate specific co-factor for the hydrolysis of GM$_2$ ganglioside by β-hexosaminidase A. This assay (described in detail in Meier et al., J. Biol. Chem., 266:1879–1887, 1991) requires that the activator has a functional hydrophobic binding site. The fluorescence dequenching assay demonstrates that the same site in the activator binds the hydrophobic R-18 dye, GM$_2$ ganglioside and PAF. When the activator containing the His$_6$-tag (i.e. activator made in bacteria) was compared with the wild-type glycosylated precursor activator form (a form expressed in CHO cells) using this conventional assay, the activator containing the His$_6$-tag functioned in a similar manner to the wildtype activator in terms of specific activity.

We claim:

1. A dosage form of an anti-inflammatory composition, said anti-inflammatory composition comprising $GM_2$ activator protein, or an anti-inflammatory $GM_2$ activator peptide derived from the $GM_2$ activator protein, in combination with at least one pharmaceutically acceptable carrier, wherein the composition comprises $GM_2$ activator protein or peptide in an amount ranging from about 1–100 mg.

2. A dosage form as defined in claim 1, wherein said anti-inflammatory composition comprises $GM_2$ activator protein.

3. A dosage form as defined in claim 2, wherein said protein comprises the amino acid sequence of residues 32–193 of SEQ. ID NO. 1.

4. A dosage form as defined in claim 1, wherein said dosage form is a sustained release oral dosage form.

5. A dosage form as defined in claim 1, wherein said dosage form is an aerosol.

6. A dosage form as defined in claim 1, wherein said dosage form is a suppository.

7. An article of manufacture comprising packaging material and an anti-inflammatory composition contained within said packaging material, wherein said composition is therapeutically effective to inhibit PAF in a mammal, and wherein the packaging material comprises a label which indicates that the composition can be used as an anti-inflammatory in a mammal, said composition comprising $GM_2$ activator protein or an anti-inflammatory $GM_2$ activator peptide derived from the $GM_2$ activator protein in combination with a pharmaceutically acceptable carrier.

8. An article of manufacture as defined in claim 7, wherein said composition comprises $GM_2$ activator protein.

9. An article of manufacture as defined in claim 8, wherein said protein comprises the amino acid sequence of residues 32–193 of SEQ ID NO:1.

10. An article of manufacture as defined in claim 7, wherein said composition is in the form of an oral dosage form.

11. An article of manufacture as defined in claim 7, wherein said composition comprises $GM_2$ activator protein or peptide in an amount ranging from about 1–100 mg.

* * * * *

UNITED STATES PATENT AND TRADEMARK OFFICE
CERTIFICATE OF CORRECTION

PATENT NO.   : 6,423,680 B1
DATED        : June 23, 2002
INVENTOR(S)  : Rigat et al.

It is certified that error appears in the above-identified patent and that said Letters Patent is hereby corrected as shown below:

Column 2,
Line 64, please delete "GM2" and insert therefor -- $GM_2$ --;

Column 5,
Line 20, please delete "t-butyloxycarbonyl" and insert therefor -- tert-butyloxycarbonyl --;

Column 8,
Line 16, please delete "PC-LUV" and insert therefor -- $PC\text{-}LUV_8$ --.

Signed and Sealed this

Eleventh Day of March, 2003

JAMES E. ROGAN
*Director of the United States Patent and Trademark Office*